United States Patent
Bausback

(12)
(10) Patent No.: US 6,335,205 B1
(45) Date of Patent: Jan. 1, 2002

(54) METHOD AND TEST STRIP FOR DETERMINING AN ANALYTE

(75) Inventor: Jörg Bausback, Neckargemünd (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/147,018

(22) PCT Filed: Mar. 12, 1997

(86) PCT No.: PCT/EP97/01253
§ 371 Date: Sep. 11, 1998
§ 102(e) Date: Sep. 11, 1998

(87) PCT Pub. No.: WO97/34147
PCT Pub. Date: Sep. 18, 1997

(30) Foreign Application Priority Data

Mar. 13, 1996 (DE) .......................................... 196 09 838

(51) Int. Cl.[7] ............................................. G01N 33/558
(52) U.S. Cl. .......................... 436/514; 422/55; 422/56; 422/57; 422/58; 435/7.5; 435/287.1; 435/287.2; 435/287.7; 435/287.9; 435/805; 435/810; 435/970; 436/169; 436/172; 436/518; 436/525; 436/530; 436/805; 436/810
(58) Field of Search ....................... 422/55–58; 435/7.5, 435/287.1, 287.2, 287.7, 287.9, 805, 810, 970; 436/169, 172, 514, 518, 525, 530, 805, 810

(56) References Cited

U.S. PATENT DOCUMENTS 5,137,808 A * 8/1992 Ullman et al. ............... 435/7.9
5,384,264 A * 1/1995 Chen et al. ................... 436/525
5,468,648 A * 11/1995 Chandler ...................... 436/518
5,559,041 A * 9/1996 Kang et al. .................. 436/518

FOREIGN PATENT DOCUMENTS

| EP | 0 362 809 | 4/1990 |
| EP | 0 381 173 | 8/1990 |
| EP | 0 585 912 | 3/1994 |
| WO | 88/08534 | * 11/1988 |

* cited by examiner

Primary Examiner—Christopher L. Chin

(57) ABSTRACT

The invention concerns a method for the immunological determination of an analyte on a chromatographic test strip containing one or several absorbent matrices on a carrier material which are in liquid-transferring contact with one another wherein the matrices form an application zone at one end and a suction zone at the other end of the carrier material, a conjugate zone in the application zone or adjoining the application zone which contains a visually detectable, particle-labelled analyte binding partner, a chromatographic zone adjoining the conjugate zone and a capture zone between the chromatographic zone and suction zone wherein the capture zone contains solid phase-bound binding partners for the analyte or for an unlabelled analyte-specific binding partner by applying the analyte solution to the application zone and measuring the bound label in the capture zone as a measure of the analyte characterized in that a fluorescent dye is applied to the application zone or to a matrix between the application zone and the capture zone which is able to migrate chromatographically in the analyte solution through the capture zone and in that the presence of the directly labelled binding partner in the capture zone is measured visually during simultaneous excitation of the fluorescent dye located in the region of the capture zone.

24 Claims, No Drawings

METHOD AND TEST STRIP FOR DETERMINING AN ANALYTE

The invention concerns a determination method for an analyte on a chromatographic test strip using particle-labelled binding partners and a corresponding test strip.

For some time chromatographic analytical elements or test strips have also been used to an increasing extent to detect analytes with the aid of analyte-specific binding partners. These test elements have been successfully used especially in immunoassays since a so-called bound/free separation can rapidly take place due to the chromatographic migration of the analyte solution. For this a labelled binding partner is bound directly or indirectly when it passes a capture reagent in amounts that depend on the amount of the analyte and can thus be determined in this manner. Such test strips and determination methods are described among others in EP-A-0 186 799, EP-A-0 291 194, EP-A-0 323 605 and EP-A-0 250 137.

Recently increasing use has been made of so-called directly labelled binding partners for detection since, in contrast to enzyme-labelled binding partners, their label can be detected directly without addition of an enzyme substrate. In this case labels are advantageous which can be seen with the naked eye, in particular particulate insoluble labels such as dyed latex, coloured sols and metal sols especially gold. In chromatographic immunoassays these direct labels are fixed by immobilized binding partners in a capture zone when the analyte is present and are measured visually as a measure for the presence of the analyte. These capture reagents are preferably accommodated in a small space as a line in order to achieve a higher concentration of the directly labelled binding partners. When an analyte is present a coloured line forms in the line-shaped capture zone which can be observed with the naked eye.

It has turned out that the human eye has difficulties in distinguishing whether a line has formed or not in the capture zone especially with low amounts of analyte. In particular when the lighting conditions are poor a colouration in the capture zone is not noticed and so a false-negative result is read.

The object of the invention was therefore to provide a method and an analytical element which enables a reliable visual reading on a chromatographic test element using visually detectable, particle-labelled binding partners especially under inadequate lighting conditions and/or at low analyte concentrations. On the other hand the method should not adversely influence or interfere with the readings under normal daylight. The object is achieved by the invention as set out in the claims.

The invention concerns a method for the immunological determination of an analyte on a chromatographic test strip containing one or several absorbent matrices on a carrier material which are in liquid-transferring contact with one another wherein the matrices form an application zone at one end and a suction zone at the other end of the carrier material, a conjugate zone in the application zone or adjoining the application zone which contains a visually detectable, particle-labelled analyte binding partner, a chromatographic zone adjoining the conjugate zone and a capture zone between the chromatographic zone and suction zone wherein the capture zone contains solid phase-bound binding partners for the analyte or for an unlabelled analyte-specific binding partner by applying the analyte solution to the application zone and measuring the bound label in the capture zone as a measure of the analyte characterized in that a fluorescent dye is applied to the application zone or to a matrix between the application zone and the capture zone which is able to migrate chromatographically in the analyte solution through the capture zone and in that the presence of the directly labelled binding partner in the capture zone is measured visually on the basis of the contrast that is formed during simultaneous stimulation of the fluorescent dye located in the region of the capture zone.

A further subject matter of the invention is a chromatographic test strip containing one or several absorbent matrices on a carrier material in liquid-transferring contact with one another in which the matrices form an application zone at one end and a suction zone at the other end of the carrier material, a conjugate zone in the application zone or adjoining the application zone which contains a visually detectable, particle-labelled analyte binding partner, a chromatographic zone adjoining the conjugate zone and a capture zone between the chromatographic zone and suction zone wherein the capture zone contains solid phase-bound binding partners for the analyte or for an unlabelled analyte-specific binding partner characterized in that a fluorescent dye is applied to the application zone or to a matrix between the application zone and capture zone which is able to migrate chromatographically in the analyte solution.

The test strip contains one or several absorbent matrices on a carrier material which are essentially arranged next to one another and which form the various zones. It is possible that several matrices are present in one zone that are made of the same or different materials. In the case of the application zone and the conjugate zone these can be arranged one behind the other and be composed of one or different matrix materials. However, the application zone and conjugate zone may also be identical and be composed of one and also of several matrices lying on top of each other.

Matrices are understood as capillary-active, absorbent, preferably porous materials which can be fibrous or non-fibrous.

Suitable carrier materials are layers or strips of glass, metal or plastic. Strips of plastic foils such as polystyrene have proven to be particularly preferable.

The matrices can be attached to the carrier material using double-sided adhesive tape. However, hot-melt adhesive is preferably used.

The matrices are arranged on the carrier material in such a way that they form a liquid transport path and liquid that is applied to the matrix or the matrices of the sample application zone reaches, through capillary forces, the suction zone via the conjugate zone, the chromatographic zone and the capture zone. For this it is necessary that the various matrices are in liquid contact with one another. This can be achieved when the edges of the matrices touch one another. However, more advantageously the matrices partially overlap.

In order to transport an amount of liquid through the capture zone which is adequate for the detection of analytes in particularly low concentration, it has proven to be advantageous that the chromatographic material that adjoins the capture zone is able to take up as much as possible of the liquid passing through the capture zone. It is particularly advantageous when this material (suction zone) can take up so much liquid that most or preferably the entire analyte liquid can pass through the capture zone.

Specifically binding substances are used in the test carrier in order to detect analytes in low concentrations. These are understood as components of a specific binding pair. Specific binding pairs are for example lectins and corresponding saccharides, DNA or RNA and corresponding complementary DNA or RNA or antigens and antibodies or antibody fragments that bind to them. Biotin or streptavidin are also a specific binding pair. Within the present invention particular consideration is given to the use of antibodies or antibody fragments for the detection of antigens. However, a person skilled in the art can easily apply these embodiments to other specific binding pairs.

Particle-labelled, analyte-specific binding partners (conjugates) that can migrate are impregnated in the conjugate zone which can be located in or adjoin the sample application zone. In the present invention this label should be visually detectable with the naked eye under normal light. Particles as a label are understood as insoluble particles preferably with a size of 1–100 nm. Especially preferred are coloured latex, coloured liposomes, selenium, tellurium, carbon black, coloured sols, metal sols; gold is especially preferred.

The amount of the labelled, analyte-specific binding partner should be preferably in excess over the expected amount of analyte.

Absorbent and above all porous plastic layers or membranes have proven to be suitable as a conjugate material e.g. paper, fleeces, porous plastic layers or membranes. Fibrous matrices which contain large amounts of glass fibres or/and synthetic fibres such as for example polyester fibres and/or synthetic wool have proven to be particularly suitable. Fleeces as described in EP-A-0 326 135 are especially preferable. If two or several matrices are present in the sample application zone it is preferable that they essentially lie one on top of the other.

A capture reagent is immobilized in the capture zone. This can, on the one hand, be an analyte-specific binding partner. However, it can also be a binding reagent for a soluble migratable unlabelled analyte binding partner applied to the test strip on the application zone or between the application zone and capture zone. It has proven to be preferable when the capture reagent is streptavidin which can bind a freely mobile, applied biotinylated analyte binding partner when it passes through the streptavidin zone.

The capture reagent can be immobilized according to methods known to a person skilled in the art e.g. covalently immobilized (cf. e.g. EP-A-0 374 778). Cellulose nitrate or nitrocellulose ester has also proven to be suitable as the matrix for the capture zone since very many substances e.g. proteins or nucleic acids are absorptively bound so strongly to these materials that a chemical bond is not necessary for the immobilization.

In order to achieve the highest possible colour density of the labelled binding partners captured in the capture zone it is particularly advantageous to apply the capture reagent in a high density in the smallest possible dimension relative to the direction of chromatography. Hence it is preferable to immobilize the capture reagent in the capture zone as a thin line or band perpendicular to the lengthwise direction of the test strip.

Lines with a width of several tenths of a mm to several mm, preferably 0.5–1 mm width, have proven to be extremely suitable for the detection of analytes at concentrations of about $10^{-12}$ mol/l. The capture reagent can be applied by line dosing by means of a cannula, by ink-jet or airbrush.

In this connection it is advantageous that the amount of capture reagent is at least 1 $\mu$g/cm$^2$ and particularly preferably up to 40 $\mu$g/cm$^2$.

According to the invention a fluorescent dye is impregnated in a soluble form in the application zone or between the application zone and capture zone when or before the analyte is applied to the sample application zone. This fluorescent dye should be easily excitable by external light sources e.g. under a UV lamp and preferably emit in the visual range. Furthermore the fluorescent dye must chromatograph on the test strip together with the analyte solution. If the fluorescent dye is not applied together with the analyte solution it is advantageous to apply it over a large area perpendicular to the direction of chromatography so that after completion of the chromatography of the analyte solution it covers at least a region before and after the capture zone. The site between the application zone and capture zone on which the fluorescent dye is applied over an area should be selected such that the fluorescent dye co-chromatographs in the analyte liquid such that after completion of the chromatography the fluorescent dye is located on both sides of the capture zone. A person skilled in the art can, without much work, establish the impregnation site and the impregnation area on one of the test strip matrices in front of the capture zone depending on the solubility and chromatographic properties of a selected fluorescent dye.

Particularly suitable fluorescent dyes are AMF (aminomethylfluorescein), 5(6)-carboxyfluorescein-N-hydroxy-succinimide ester (Fluos), acridine orange, Texas red, rhodamine or resorufin.

The fluorescent dye should have no or only a relatively low colour under daylight or optionally have a colouration that is different from the colour of the direct label. In contrast to the directly-labelled conjugate, the fluorescent dye is not present conjugated to immunological binding partners. Furthermore the fluorescent dye should not influence the immunological reaction.

In order to carry out the immunoassay sample liquid is applied to the sample application zone. The sample liquid can be mixed with the fluorescent dye. However, the fluorescent dye is preferably impregnated on the test strip before application of the sample liquid.

In a sandwich immunoassay the analyte forms a sandwich complex with the labelled analyte binding partner and with a second non-labelled analyte binding partner during the chromatography of the analyte solution towards the capture zone. This is either immobilized in the capture zone or, having been provided with a specific binding site for a capture reagent of the capture zone, is impregnated in a soluble manner between the application zone and capture zone. Non analyte-bound, labelled binding partners pass through the capture zone while labelled binding partners that are bound via the analyte are bound in the capture zone and their colour indicates the presence of analyte.

According to the invention fluorescent dye dissolved in the analyte solution chromatographs with the analyte solution at least until part of the fluorescent dye, but not the entire amount of fluorescent dye, passes the capture zone and thus surrounds both sides of the capture zone after the end of the chromatography.

When the capture zone is irradiated with light of a suitable fluorescence excitation wavelength, for example UV light, it has surprisingly turned out that when the analyte is present the non-fluorescent particle label bound to the capture zone stands out very strongly against the fluorescent background formed by the fluorescent dye, for example as a black line. In the case of low amounts of analyte this enables the presence of considerably smaller amounts of solid phase-bound label to be detected with the naked eye especially under inadequate lighting conditions by simple illumination of the test strip using a fluorescent lamp than would have been possible without this fluorescence contrast amplification.

On the other hand it was surprising that in the absence of analyte contrast differences between the capture zone and the fluorescent background bordering in front of and behind the capture zone which may lead to false-positive results did not occur at all. The capture zone containing the unlabelled solid phase-bound binding partner together with the area in front of it and behind it appears under fluorescent light to be uniformly fluorescent in the absence of the analyte.

A further advantage of the contrast amplification according to the invention is that the fluorescent dye results in no interferences at all when the capture zone is detected visually under normal light. Consequently the analytical method according to the invention can be optionally carried out according to the prior art without fluorescence excitation (if for example a UV lamp is not available) without loss of quality or according to the invention by fluorescence excitation with contrast amplification.

The method according to the invention enables the presence of very low concentrations of analytes to be detected of the order of magnitude of $10^{-10}$–$10^{-12}$ mol/l.

What is claimed is:

1. A chromatographic test strip for determining an analyte in an analyte solution, comprising
    at least one absorbent matrix located on a carrier material and defining a plurality of zones each in liquid-transferring contact with the adjacent zone(s), the plurality of zones having an application zone at one end and a suction zone at the other end,
    a conjugate zone located in the application zone or adjoining the application zone and containing a visually detectable, particle-labelled analyte binding partner,
    a chromatographic zone adjoining the conjugate zone,
    a capture zone located between the chromatographic zone and the suction zone and containing solid phase-bound binding partners for the analyte or for an unlabelled analyte-specific binding partner, and
    a fluorescent dye located in the application zone or in a zone between the application zone and the capture zone and formed to migrate chromatographically in the analyte solution at least partly through the capture zone and to provide fluorescence contrast amplification of the particle label when the particle label is bound in the capture zone.

2. The test strip of claim 1, wherein an unlabelled, migratable, analyte-specific binding partner which has a binding site for the solid phase-bound binding partner is located in the application zone or between the application zone and the capture zone.

3. The test strip of claim 1, wherein the capture zone is in the form of a line.

4. The test strip of claim 1, wherein the label is a metal sol.

5. The test strip of claim 4, wherein the label is gold.

6. The test strip of claim 1 wherein streptavidin is the solid phase-bound binding partner immobilized in the capture zone and the unlabeled analyte-specific binding partner is a biotin-labeled binding partner for the analyte.

7. The test strip of claim 1, wherein the fluorescent dye is impregnated in the application zone.

8. The test strip of claim 1, wherein the fluorescent dye is impregnated in the conjugate zone.

9. The test strip of claim 1, wherein the fluorescent dye is aminophenylfluorescein.

10. The test strip of claim 1 wherein the fluorescent dye has no color under daylight.

11. The test strip of claim 1 wherein the fluorescent dye is excitable by UV light.

12. The test strip of claim 1 wherein the fluorescent dye has a coloration different from the color of the direct label.

13. A test strip for determining the presence of an analyte in a solution, the test strip comprising:
    at least one absorbent matrix defining zones, each zone being in liquid-transferring contact with at least one adjacent zone and having an application zone and a suction zone located downstream of the application zone,
    a conjugate zone located upstream of the suction zone, the conjugate zone containing a visually detectable, particle-labelled analyte binding partner,
    a chromatographic zone adjoining the conjugate zone,
    a capture zone located between the chromatographic zone and the suction zone and containing solid phase-bound binding partners for the analyte or for an unlabelled analyte-specific binding partner, and
    a fluorescent dye located upstream of the capture zone, the fluorescent dye being formed to migrate chromatographically in the analyte solution at least partly through the capture zone and to provide fluorescence contrast amplification of the particle label when the particle label is bound in the capture zone.

14. The test strip of claim 13 wherein an unlabelled, migratable, analyte-specific binding partner which has a binding site for the solid phase-bound binding partner is located in the application zone or between the application zone and the capture zone.

15. The test strip of claim 13 wherein the capture zone is in the form of a line.

16. The test strip of claim 13 wherein the label is a metal sol.

17. The test strip of claim 13 wherein the label is gold.

18. The test strip of claim 13 wherein streptavidin is the solid phase-bound binding partner immobilized in the capture zone.

19. The test strip of claim 13 wherein the fluorescent dye is impregnated in the application zone.

20. The test strip of claim 13 wherein the fluorescent dye is impregnated in the conjugate zone.

21. The test strip of claim 13 wherein the fluorescent dye is aminophenylfluorescein.

22. The test strip of claim 13 wherein the fluorescent dye has no color under daylight.

23. The test strip of claim 13 wherein the fluorescent dye is excitable by UV light.

24. The test strip of claim 13 wherein the fluorescent dye has a coloration different from the color of the direct label.

* * * * *